United States Patent
Opsal

(10) Patent No.: US 6,836,328 B2
(45) Date of Patent: *Dec. 28, 2004

(54) DETECTOR CONFIGURATIONS FOR OPTICAL METROLOGY

(75) Inventor: Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/696,269

(22) Filed: Oct. 29, 2003

(65) Prior Publication Data

US 2004/0085539 A1 May 6, 2004

Related U.S. Application Data

(63) Continuation of application No. 10/137,606, filed on May 2, 2002, now Pat. No. 6,678,046.
(60) Provisional application No. 60/315,514, filed on Aug. 28, 2001.

(51) Int. Cl.[7] .............................................. G01B 11/06
(52) U.S. Cl. ..................................... 356/369; 356/632
(58) Field of Search ................................. 356/364–369, 356/630–632; 250/225, 559.27, 559.19

(56) References Cited

U.S. PATENT DOCUMENTS

| | | | | |
|---|---|---|---|---|
| 3,992,105 A | 11/1976 | White | ........................ | 356/369 |
| 4,053,232 A | 10/1977 | Dill et al. | ................... | 356/369 |
| 4,158,506 A | 6/1979 | Collett | ........................ | 356/365 |
| 4,286,843 A | 9/1981 | Reytblatt | .................... | 359/489 |
| 4,999,014 A | 3/1991 | Gold et al. | .................. | 356/382 |
| 5,042,951 A | 8/1991 | Gold et al. | .................. | 356/369 |
| 5,166,752 A | 11/1992 | Spanier et al. | .............. | 356/369 |
| 5,181,080 A | 1/1993 | Fanton et al. | ............... | 356/381 |
| 5,329,357 A | 7/1994 | Bernoux et al. | ............. | 356/369 |
| 5,412,473 A | 5/1995 | Rosencwaig et al. | ....... | 356/351 |
| 5,596,411 A | 1/1997 | Fanton et al. | ............... | 356/369 |
| 5,608,526 A | 3/1997 | Piwonka-Corle et al. | ... | 356/369 |
| 5,889,593 A | 3/1999 | Bareket | ...................... | 356/445 |
| 6,278,519 B1 | 8/2001 | Rosencwaig et al. | ....... | 356/369 |
| 6,678,046 B2 * | 1/2004 | Opsal | ......................... | 356/369 |
| 2002/0038196 A1 | 3/2002 | Johnson et al. | ............. | 702/179 |

FOREIGN PATENT DOCUMENTS

JP 6-117935 4/1994 ............. G01J/4/04

OTHER PUBLICATIONS

J.M. Leng et al., "Characterization of titanium nitride (TiN) films on various substrates using spectrophotometry, beam profile reflectometry, beam profile ellipsometry and spectroscopic beam profile ellipsometry," *Thin Solid Films*, vol. 313–314, 1998, pp. 308–313.

* cited by examiner

*Primary Examiner*—Hoa Q. Pham
(74) *Attorney, Agent, or Firm*—Stallman & Pollock LLP

(57) ABSTRACT

An apparatus is disclosed for obtaining ellipsometric measurements from a sample. A probe beam is focused onto the sample to create a spread of angles of incidence. The beam is passed through a quarter waveplate retarder and a polarizer. The reflected beam is measured by a detector. In one preferred embodiment, the detector includes eight radially arranged segments, each segment generating an output which represents an integration of multiple angle of incidence. A processor manipulates the output from the various segments to derive ellipsometric information.

9 Claims, 4 Drawing Sheets

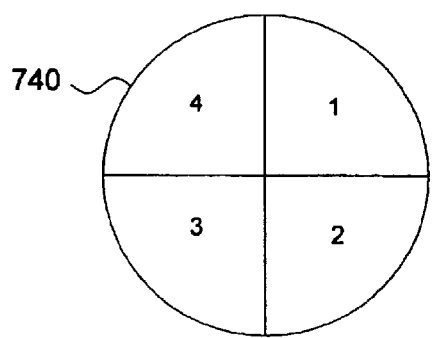
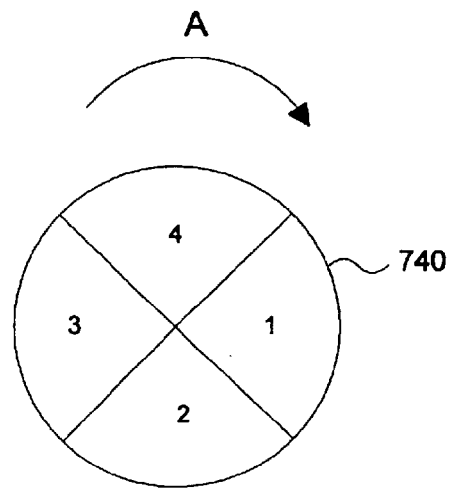
FIGURE 7A  FIGURE 7B
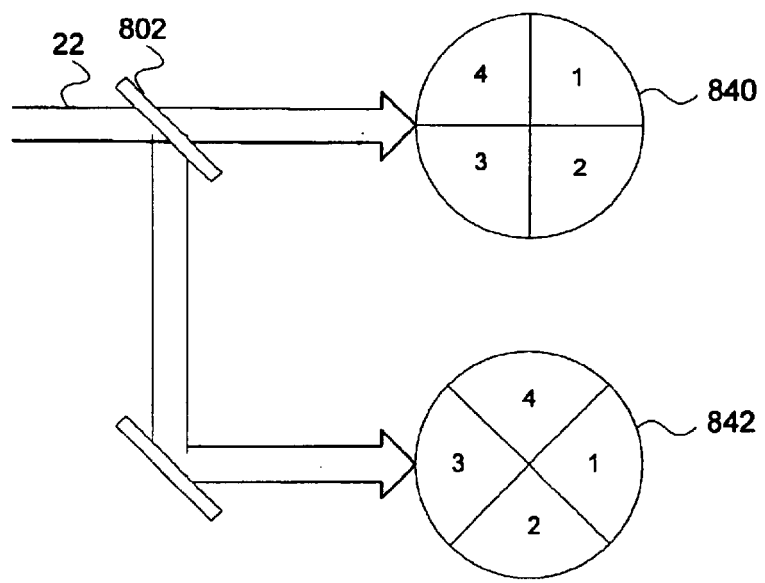
FIGURE 8

US 6,836,328 B2

1

DETECTOR CONFIGURATIONS FOR OPTICAL METROLOGY

PRIORITY

This application is a continuation of U.S. Ser. No. 10/137,606, filed May 2, 2002 now U.S. Pat. No. 6,678,046, which claimed priority to Provisional Application Ser. No. 60/315,514, filed Aug. 28, 2001, the disclosure of which is incorporated herein by reference.

BACKGROUND OF THE INVENTION

There is ongoing interest in expanding and improving the measurement of semiconductor wafers. A number of optical metrology tools have been developed for non-destructively evaluating the characteristics of thin films formed on semiconductors during the fabrication process. More recently, optical metrology systems have been proposed for analyzing the geometry of small periodic structures (critical dimensions) on semiconductors.

Typical optical tools include reflectometry (both single wavelength and spectroscopic) and ellipsometry (again, both single wavelength and spectroscopic.) In some metrology tools, these various techniques are combined. See for example U.S. Pat. Nos. 6,278,519 and 5,608,526, the disclosures of which are incorporated herein by reference.

Other metrology tools have been developed which rely on measurements at multiple angles of incidence (both single wavelength and spectroscopic). One class of such systems have been commercialized by the Assignee herein are capable of deriving information about multiple angles of incidence simultaneously. In these systems, a strong lens (high numerical aperture) is used to focus a probe beam of light onto the sample in a manner to create a spread of angles of incidence. An array detector is used to measure the reflected rays of the probe beam as a function of the position within the probe beam. The position of the rays within the probe beam corresponds to specific angles of incidence on the sample. Theses systems are disclosed in U.S. Pat. Nos. 4,99,014 and 5,042, 951, incorporated herein by reference. U.S. Pat. No. 4,99,014 related to reflectometry while U.S. Pat. No. 5,042, 951 relates to ellipsometry. (See also, U.S. Pat. No. 5,166,752, also incorporated herein by reference).

In a variant on this system, U.S. Pat. No. 5,181,080 (incorporated by reference), discloses a system in which a quad-cell detector (FIG. 1) is used to measure the reflected probe beam. Each quadrant 1–4 of the detector measures an integration of all of the angles of incidence falling on the sample. By subtracting the sums of opposite quadrants, ellipsometric information can be obtained. As described in the latter patent, the information derived from the analysis corresponds to the ellipsometric parameter delta δ which is very sensitive to the thickness of very thin films on a sample.

The concepts of the latter patents were expanded to provide spectroscopic measurements as described in U.S. Pat. No. 5,412,473, also incorporated herein by reference. In this patent, the system was modified to include a white light source. In one approach, a color filter wheel was used to sequentially obtain multiple wavelength information. In another approach, a filter in the form of a rectangular aperture was used to select a portion of the reflected beam. This portion was then angularly dispersed onto an array with each row providing different wavelength information and each column containing the various angle of incidence information.

U.S. Pat. No. 5,569,411, also incorporated by reference, disclosed a preferred approach for obtaining spectroscopic information for an integrated multiple angle of incidence system of the type described in U.S. Pat. No. 5,181,080 discussed above. In this approach, a filter was provided that transmitted light along one axis and blocked light along an orthogonal axis. The transmitted light was angularly dispersed and measured to provide spectroscopic information along one axis of the probe beam. The filter was then rotated by ninety degrees to obtain measurements along the remaining axis. Various modifications of this approach were discussed, including splitting the beam and using two identical filters disposed orthogonal to each other to obtain both measurements simultaneously. (See also "Characterization of titanium nitride (TiN) films on various substrates using spectrophotometry, beam profile reflectometry, beam profile ellipsometry and spectroscopic beam profile ellipsometry," Leng, et. al., *Thin Solid Films*, Volume 313–314, 1998, pages 309 to 313.)

The integrated multiple angle ellipsometric measurement system described in U.S. Pat. No. 5,181,080, cited above has been successfully commercialized and is incorporated into the Opti-Product sold by the Assignee herein. The technology is marketed under the trademark Beam Profile Ellipsometry. (See U.S. Pat. No. 6,278,519 cited above.) As described in the '080 patent, the four segments of the quad cell detector can be summed to provide information about the total reflected power of the probe beam. In addition, the sum of the output of the quadrants along one axis can be subtracted from the sum of the outputs of the remaining two quadrants to provide a result which is corresponds to the ellipsometric parameter δ.

This arrangement provides valuable information that can be used to determine the thickness of thin films. However, the limited information from this type of detection cannot typically be used to derive both of the ellipsometric parameters, Ψ and δ. U.S. Pat. No. 5,586,411, discloses that it would be possible to derive such information if one of polarizers were rotated and multiple measurements taken. As noted therein at column 12, line 48, if enough measurements are taken, a Fourier analysis can be performed on the data allowing the parameters of Ψ and δ to be extracted.

When designing commercial inspection systems, it is often desirable to minimize the number of moving parts. For example, moving parts often create particulates that can contaminate the wafer. To the extent parts must be moved, the motion systems must have high precision. Further, movements of parts that are specifically designed to modify optical properties, such as retarders or polarizers can effect how the system transmits and detects light.

Therefore, it is an object of the present invention to enhance the operation of an integrated, simultaneous multiple angle ellipsometric system without the drawbacks of the prior approaches. In particular, the subject invention is intended to permit the derivation of additional ellipsometric information, including both δ and Ψ. In one class of embodiments, this additional information is derived in a system with an improved detector arrangement without the need for moving parts. In another class of embodiments, the rotating element is limited to the detector which does not effect the polarization or retardation of the light.

SUMMARY OF THE INVENTION

In a first embodiment, a narrowband light source such as a laser is used to generate a probe beam. The polarized beam is focused onto the sample in a manner to create a large spread of angles of incidence. The probe beam light is passed through a quarter waveplate for retarding the phase of one of the polarization states of the beam with respect to the other polarization state of the beam. A polarizer is provided for creating interference between the two polarization states in the reflected probe beam.

In accordance with the subject invention, a detector is provided with eight segments radially arranged around a center axis. In one embodiment, eight pie shaped sections are provided in a configuration which is essentially a quad cell with each quadrant further divided in half. In another embodiment, the eight segments are arranged in an annular ring.

In either case, the output of the segments lying substantially along one radial axis is subtracted from the output of the segments lying substantially along an orthogonal radial axis. In order to gain additional information, the output of the sectors lying along a third radial axis located midway between the first two orthogonal axes (i.e. at 45 degrees) is subtracted from the sectors lying along a fourth radial axis, perpendicular to the third axis. This extra information obtained corresponds to an orientation essentially shifted by 45 degrees from the first measurements. When all the measurements are combined, the sample may be more accurately evaluated. This extra information can be supplied to conventional fitting algorithms to evaluate characteristics including thin film thickness, index of refraction and extinction coefficient. In addition, geometrical parameters of structures formed on semiconductors such as line width, spacing, and side wall angle and shape can also be evaluated. These calculations can be made using the measurements directly. Alternatively, the measurements can be used to derive the ellipsometric parameters $\Psi$ and $\Delta$ which are then used to evaluate the sample.

The use of an eight segment detector allows the extra measurement to be obtained simply by summing and subtracting outputs of the sectors in the processor. Other arrangements can be used to provide equivalent results. For example, the reflected beam could be split into two parts and the two quadrant detectors use, one offset by 45 degrees from the other. Alternatively, a single rotatable quadrant detector could be used. After the first measurement is made, the detector could be rotated by 45 degrees and a second measurement could be made. In a preferred embodiment, the output of all the segments is summed to provide a measure of the full power of the reflected beam.

It may also be possible to rotate the either the polarizer or the retarder to achieve a similar result.

The concept can also be extended to the use of a two dimensional detector array. Using a processor, the elements on the array can be computationally mapped to the eight segment and the analysis can be made as described above. This approach can be particularly useful for measurement of critical dimensions, where the orientation of the sample structure and orientation of the probing radiation is significant and possibly difficult to control.

The subject invention can also be extended to spectroscopic measurements. In this case, a white light source would typically be used to generate a polychromatic probe beam. The probe beam could be passed through a color filter or monochrometer which sequentially transmits narrow bands of wavelengths. The filter or monochrometer would preferably be located before the sample.

If simultaneous multiple wavelength information is desired, it is believed that the approach described in U.S. Pat. No. 5,596,411, which included a rotating quadrant filter, grating and array detector would be more suitable than the approach described herein.

Further objects of the subject invention can be understood with reference to the following detailed description, taken in conjunction with the drawings in which:

BRIEF DESCRIPTION OF THE DRAWINGS

FIGS. 7A and 7B are a schematic diagrams of a rotatable quadrant detector which can be used to implement the subject invention.

FIG. 8 is a schematic diagram of a pair of quadrant detectors which can be used to implement the subject invention.

DETAILED DESCRIPTION OF THE PREFERRED EMBODIMENTS

Figure 2:
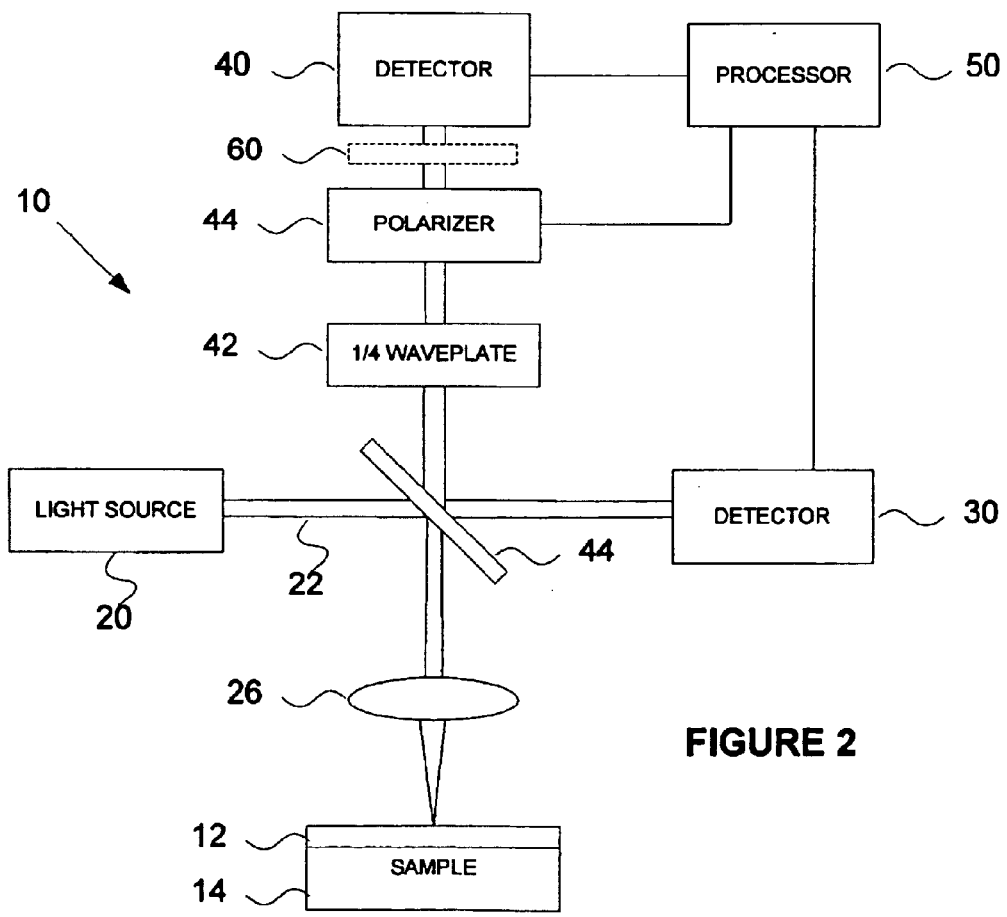
FIG. 2 is a schematic diagram of the optical lay-out of an apparatus for performing the method of the subject invention.

Turning to FIG. 2, an apparatus 10 is illustrated for performing the method of the subject invention. The apparatus lay out for this embodiment is essentially the same as that described in U.S. Pat. No. 5,181,080, except that the detector is configured with eight segments (FIG. 3) rather than four segments as in the prior art (FIG. 2). The apparatus is designed to evaluate characteristics at the surface of a sample 14, such as thin film layers 12 and/or structural features such as critical dimensions.

In this embodiment, apparatus 10 includes a light source 20 for generating a probe beam 22 of radiation. One suitable light source is a solid state laser diode which emits a linearly polarized beam having a stable, known and relatively narrow bandwidth. Probe beam 22 is turned towards the sample 14 with a 50/50 beam splitter 44. The probe beam is focused onto the surface of the sample with a lens 26. In the preferred embodiment, lens 26 is defined by a spherical, microscope objective with a high numerical aperture on the order of 0.90 NA. The high numerical aperture functions to create a large spread of angles of incidence with respect to the sample surface. The spot size is on the order of twenty microns or less and is preferably five microns or less in diameter.

In should be noted that in this illustrated embodiment, the beam is directed substantially normal to the surface of the sample prior to being focused by lens 26. This configuration helps minimize the spot size on the sample. It is within the scope of the subject invention to direct the beam at a non-normal angle of incidence to the sample as shown in U.S. Pat. No. 5,166,752. Although using an off-axis beam increases the spot size on the sample, high angles of incidence can be created with a lower numerical aperture lens.

Turning back to FIG. 1, a fraction of the probe beam power also passes through splitter 24 and falls on an incident power detector 30. As is well known to those skilled in the art, incident power detector 30 is provided to monitor fluctuations in the output power of the probe beam light source. As discussed in U.S. Pat. 5,181,080, the incident power detector can be modified to minimize measurement errors which arise due to asymmetries of the beam.

Light reflected from the surface of the sample passes up through splitter 24 towards photodetector 40. Prior to reaching detector 40, the beam 22 is passed through a quarter-wave plate 42 for retarding the phase of one of the polarization states of the beam by 90 degrees. It should be noted that the quarter-wave plate could be located in the beam path prior to the probe beam striking the sample so that the system would operate with circularly polarized light. The latter approach might have some advantages in reducing the aberrations created by lens 26. In addition, while a phase retardation of 90 degrees will maximize the desired signal, other intermediate levels of retardation would be possible.

The beam is then passed through a linear polarizer 44 which functions to cause the two polarization states of the beam to interfere with each other. In order to maximize the desired signal, the axis of the polarizer should be oriented at an angle of 45 degrees with respect to the fast and slow axes of the quarter-wave plate 42.

Figure 3:
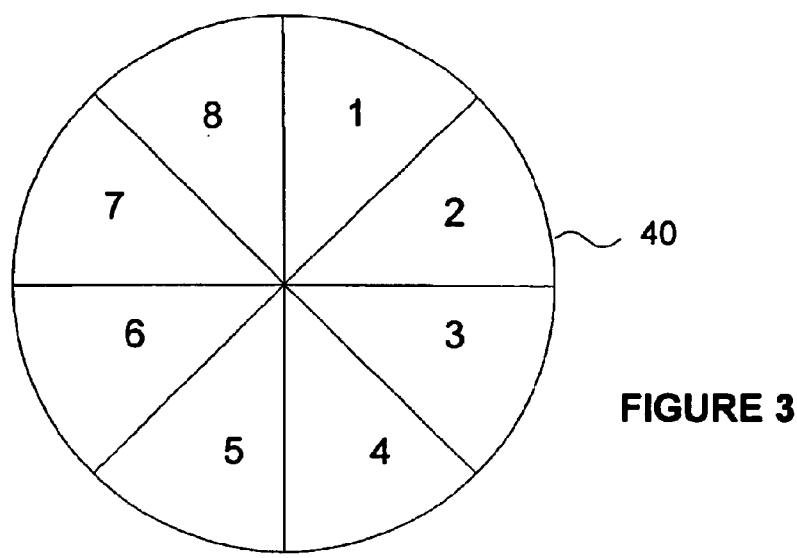
FIG. 3 is a schematic diagram of an eight segment detector for use with the subject invention.

In accordance with the subject invention, detector 40 is configured to generate independent signals from regions along two pairs of mutually orthogonal axes. In this first embodiment, this goal is achieved by using a photodetector having eight pie shaped segments. As illustrated in FIG. 3, the detector surface includes eight, radially disposed segments 1–8. Each segment will generate an output signal proportional to the magnitude of the power of probe beam striking that quadrant. This signal represents an integration of the intensities of all the rays having different angles of incidence with respect to the sample surface. While this integration approach results in the loss of some information content as compared to an analysis of individual rays, the composite approach does provide significantly greater sensitivity through enhanced signal to noise performance.

The probe beam 22 should be centered on the detector 40 so that each segment intercepts an equal portion of the probe beam. The probe beam should underfill the detector.

The output of the segments is supplied to the processor 50 for evaluation. As in the prior art, the outputs of all the segments can be summed to provide a measure of the full power of the reflected beam. As discussed below, this full power measurement can be used as an input to a regression analysis to determine the characteristics of the sample.

In accordance with the invention herein, the processor can also generate measurements which allow additional ellipsometric information to be derived as compared to the prior art approach. This difference can best be understood by comparing the two approaches.

In general, one measures the total reflectivity of the sample in accordance with the following equation:

$$R = \tfrac{1}{2}(|r_p|^2 + |r_s|^2)$$

The sine of the ellipsometric phase shift δ is determined by the equation:

$$\tan \psi e^{i\delta} = |r_p/r_s| e^{i\delta}$$

Figure 1:
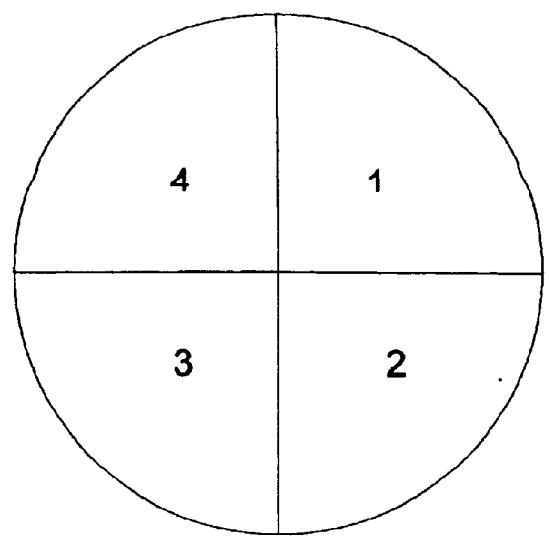
FIG. 1 is a schematic diagram of a quad-cell detector used in prior art measurements.

With the prior art detector of FIG. 1, the information is derived as follows:

$$\Sigma = 1 + 2 + 3 + 4$$

$$\Delta = (1+3) - (2+4)$$

$$R = \Sigma/\Sigma_o \text{ and } \sin\delta = \pi/2(\Delta/|r_p r_s|)$$

where $\Sigma_o$ is the measured sum signal from a known reference material.

The complete determination of the polarization state requires a measurement that gives tan ψ and that requires an additional modification to the detector as shown in FIG. 3. As noted above, the sum is formed from the outputs of the eight segments as follows:

$$\Sigma = 1+2+3+4+5+6+7+8$$

Then as previously:

$R=\Sigma/\Sigma_o$ and with $\Delta_1 \equiv (1+2+5+6) - (3+4+7+8)$ $\Delta_2 \equiv (2+3+6+7) - (4+5+8+1)$ one has $\Delta_1/\Sigma = 4/\pi(\tan \psi/\tan^2 \psi + 1)\sin \delta$ and $\Delta_2/\Sigma = -2/\pi(\tan^2 \psi - 1/\tan^2 \psi + 1)$ As can be seen, the information from the eight segments can be used to derive both Ψ and δ. In practice, those quantities may not be needed. In fact, it is often preferable to use the measurements more directly in the evaluation of sample parameters. Thus, the invention should not considered limited to determining both Ψ and δ, but rather is an approach which provides an additional measurement for analyzing the sample.

Although the measurements made by the subject apparatus could be used by themselves to characterize a sample, those measurements can also be combined with other measurement obtained from additional optical metrology devices in manner discussed in U.S. Pat. No. 6,278,519. A system with multiple inspection technologies generates a number of independent measurements which are then combined in a regression analysis to determine sample parameters.

Combining data from multiple devices is a procedure quite well known and need not be described in detail. In brief, a mathematical model is defined which describes the structure under test. A best guess of sample parameters is assigned to the model and the optical response is calculated. The calculated optical response is compared to the measured optical response. Any deviations between the calculated optical response and the measured optical response are used to vary the initial starting parameter guesses and the process is repeated in an iterative fashion until satisfactory convergence is reached. (See, for example, the Leng, article cited above.) As noted above, with such an analytical approach it is not necessary to actually calculate Ψ and δ. Rather the inputs from $\Delta_1$ and $\Delta_2$ calculations as set forth above (as well as the full power measurement) are used as inputs actual measurements to the fitting algorithm. Of course, if desired, the $\Delta_1$ and $\Delta_2$ calculations can also be used to calculate Ψ and δ if desired.

These types of analyses are suitable for both thin films and physical structures formed on the sample. It is also possible to use a database or library type approach where a set of the optical responses of a parameterized sample are calculated in advance and stored. The measured response is compared to the stored responses to determine sample parameters. (See, for example, U.S. Published applications Ser. Nos. 2002/0038186 and 2002/0035455). The subject invention is not intended to be limited either by the type of sample being measured, nor the specific algorithms used to analyze the data. As will be discussed below, there are a number of alternative detector configuration which can be used to generate the information of interest. One common thread is that measurements are taken along a first pair of orthogonal axes and along a second pair of orthogonal axes, with the second pair being perpendicular to the first pair.

Figure 4:
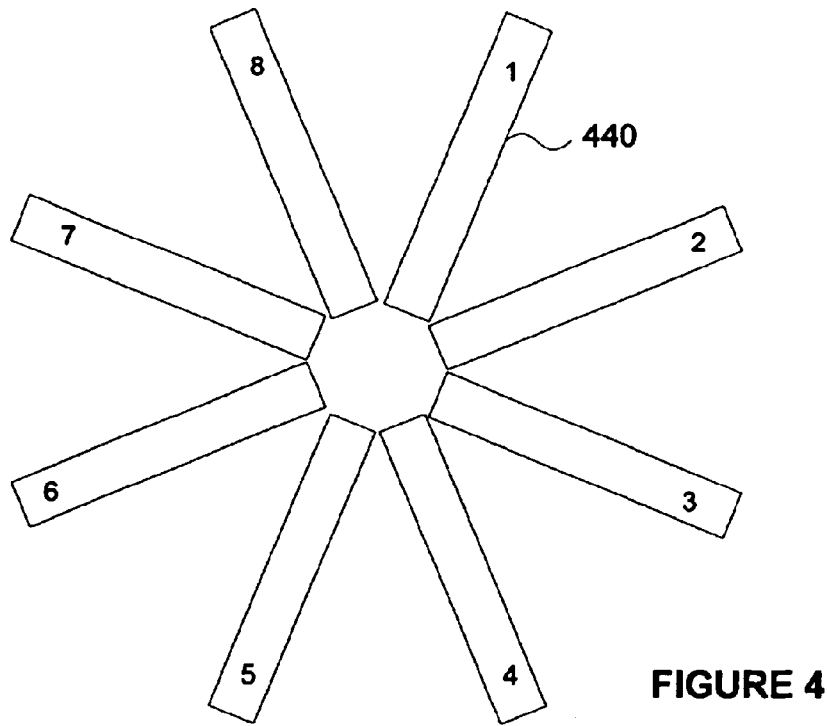
FIG. 4 is a schematic diagram of a detector having eight detector arms aligned along four axes which can be used to implement the subject invention.

FIG. 4 illustrates an alternative configuration for such a detector 440 that satisfies these criteria. Each segment 1–8 is a linear detector arranged in a star-shaped configuration that corresponds to the pie shaped segments of FIG. 3. The analysis of the measurements discussed above with respect to FIG. 3 would be identical to that of FIG. 4.

Those skilled in the art will also appreciate that segments 5 to 8 for either the FIG. 3 or FIG. 4 embodiment are complimentary to segments 1 to 4 so that a detector with only segments 1 to 4 might be used. However, adding the outputs of segments 5 to 8 to the outputs of segments 1 to 4, respectively, makes the detector insensitive to small shifts in the probe beam spot positioning and is therefore the preferred approach.

Figure 5:
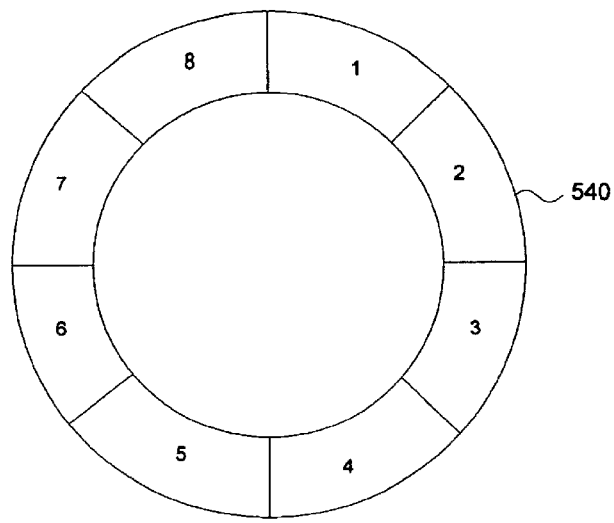
FIG. 5 is a schematic diagram of a detector having segments in the form of an annular ring which can be used to implement the subject invention.

The detector configurations of FIGS. 3 and 4 will produce a measurement that represents an average over all the incident angles. To examine a narrower range of angles of incidence, a detector 540 as shown in FIG. 5 with eight segments arranged in an annulus might be used. Such a detector might be of interest where the probe beam is directed substantially normal to the sample before focusing as shown in FIG. 2. In such a case, the radially outermost rays of the probe beam have the highest angles of incidence. The annular ring configuration of FIG. 5 would capture only those higher angle of incidence rays, which, in the case of isotropic samples, often carry the most information.

Figure 6A:
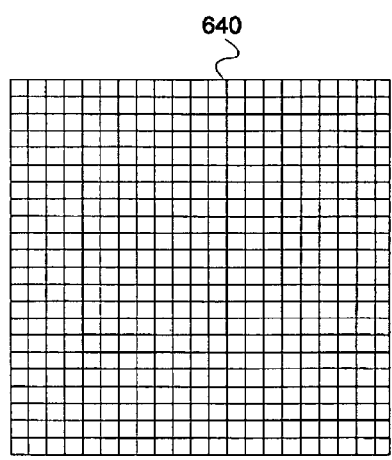
FIGS. 6A and 6B are schematic diagrams of a two dimensional detector array which can be used to implement the subject invention.
Figure 6B:
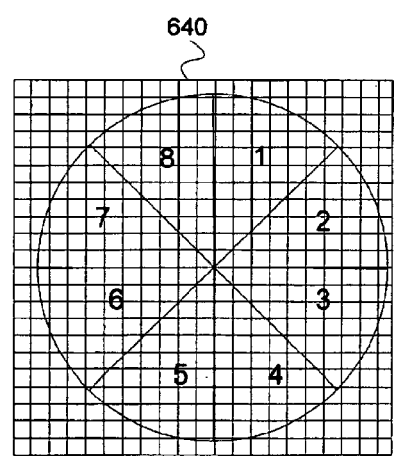

The subject invention could also be implemented using a detector 640 comprised of a two dimensional array of detector elements or pixels as shown in FIG. 6A. Such a detector could be defined by a CCD array. The pixels in the array could be mapped into eight segments to correspond to the detectors shown in FIGS. 3 to 5. The mapping of pixels to the detector segments of FIG. 3 is shown in FIG. 6B. The processor would select the output from the appropriate pixels to calculate $\Delta_1$ and $\Delta_2$ and derive the ellipsometric information.

With a sufficiently dense array almost any configuration of angles of incidence is possible. This is especially significant for measuring physical structures (CD) where the xy orientation of the sample structure and the orientation of probing radiation is relevant and significant. With a system such as described above it is possible (with minimal moving mechanisms) to probe the CD structure from all angles of incidence, planes of incidence and polarizations relative to the orientation of the CD structure.

If it is desired to extend this concept to measure multiple wavelengths, the laser light source 20 could be a white light source that would generate a polychromatic probe beam. A wavelength selective filter 60 (shown in phantom line in FIG. 1) would then be placed somewhere in the light path between the light source and the detector. The filter could take the form of simple band pass (color) filters which are selectively moved into the path of the beam. Alternatively, a monochrometer could be used to sequentially select narrow wavelength regions. Of course a tunable laser or multiple lasers with different wavelengths could also be used.

FIGS. 7 and 8 illustrate two further embodiments wherein detectors with only four quadrants can be used to obtain the measurements required herein. FIG. 7a illustrates a quadrant detector 740 positioned to take a first set of measurements. Segment 1 would generate an output equivalent to segments 1 and 2 of the detector of FIG. 3. Similarly, segment 2 of the detector of FIG. 7a would generate an output equivalent to segments 3 and 4 of the detector of FIG. 3, segment 3 of the detector of FIG. 7a would generate an output equivalent to segments 5 and 6 of the detector of FIG. 3 and segment 4 of the detector of FIG. 7a would generate an output equivalent to segments 7 and 8 of the detector of FIG. 3. This measurement would permit the calculation of $\Delta_1$.

Once this measurement is made, the quadrant detector could be rotated 45 degrees to a position shown in FIG. 7b. In this orientation, segment 1 of the detector of FIG. 7b would generate an output equivalent to segments 2 and 3 of the detector of FIG. 3. Similarly, segment 2 of the detector of FIG. 7b would generate an output equivalent to segments 4 and 5 of the detector of FIG. 3, segment 3 of the detector of FIG. 7b would generate an output equivalent to segments 6 and 7 of the detector of FIG. 3 and segment 4 of the detector of FIG. 7b would generate an output equivalent to segments 8 and 1 of the detector of FIG. 3. This measurement would permit a calculation of $\Delta_2$.

The detector configuration of FIG. 7 might be desirable to simplify and minimize the cost of the detector. However, the trade off would be that the measurement would require two steps and the rotation of an element. Rather than rotating the detector, similar results might be achieved if either the polarizer or analyzer or both were rotated to provide independent measurements.

FIG. 8 illustrates a configuration conceptually similar to FIG. 7 but which would allow both measurements to be taken at once. More specifically, after the probe beam is reflected from the sample and passes the polarizer and waveplate, it can be divided by beam splitter 802. Two separate quadrant detectors 840 and 842 are each located in one of the two beam paths. The quadrants of detector 840 are offset from the quadrants of detector 842 by 45 degrees. The output of the quadrants of detector 840 can be used calculate $\Delta_1$ and the output of the quadrants of detector 842 can be used to calculate $\Delta_2$. As an alternative, one could place the beam splitter in the path of the reflected probe but before the quarter waveplate and polarizer. In this alternative, it would be necessary to place a quarter waveplate and a polarizer in each path. In this arrangement, it would also be possible to orient both detectors at the same azimuthal angle, but have different positions for either the waveplate or the polarizer in one path as compared to the other path.

While the subject invention has been described with reference to a preferred embodiment, various changes and modifications could be made therein, by one skilled in the art, without varying from the scope and spirit of the subject invention as defined by the appended claims.

I claim:

1. An apparatus for evaluating the characteristics of sample comprising:
   a light source for generating a probe beam;
   a focusing element for focusing the beam onto the surface of the sample in manner to create a spread of angles of incidence with varying azimuthal angles;
   a retarder located in the path of the beam;
   a polarizer located in the path of the reflected beam;
   a detector in the path of the reflected beam, said detector defined by a two-dimensional array of detector elements, each element generating individual output signals; and a processor for calculating the difference between the sum of the output signals of elements lying along a first pair of orthogonal axes and the difference between the sum of the output signals of elements lying along a second pair of orthogonal axes disposed at a 45 degree azimuthal angle with respect to the first pair of axes, said processor evaluating the characteristics of the sample based on said calculations.

2. An apparatus as recited in claim 1, wherein said light source is a narrow band laser.

3. An apparatus as recited in claim 1, wherein the light source generates a polychromatic probe beam and further including a means to permit detection of the probe beam as a function of wavelength.

4. An apparatus as recited in claim 3, wherein said means is defined by a selectable color filter located in the path of the beam.

5. An apparatus for evaluating the characteristics of sample comprising:

a light source for generating a probe beam;

a focusing element for focusing the beam onto the surface of the sample in manner to create a spread of angles of incidence with varying azimuthal angles;

a retarder located in the path of the beam;

a polarizer located in the path of the reflected beam;

a detector in the path of the reflected beam, said detector defined by a two-dimensional array of detector elements, each element generating output signals; and a processor for correlating the individual output signals from the detector elements to specific angles of incidence and a plurality azimuthal positions, said azimuthal positions including two orthogonal axes and at least two more azimuthal positions intermediate the orthogonal axes, said processor evaluating the characteristics of the sample based on said correlation.

6. An apparatus as recited in claim 5, wherein the processor operates to calculate the difference between the sum of the output signals of detector elements disposed along said two orthogonal axes and the difference between the sum of the output signals of the detector elements disposed along said at least two more azimuthal positions intermediate said two orthogonal axes.

7. An apparatus as recited in claim 5, wherein said light source is a narrow band laser.

8. An apparatus as recited in claim 5, wherein the light source generates a polychromatic probe beam and further including a means to permit detection of the probe beam as a function of wavelength.

9. An apparatus as recited in claim 8, wherein said means is defined by a selectable color filter located in the path of the beam.

* * * * *